United States Patent
Bolan et al.

(10) Patent No.: US 11,241,296 B2
(45) Date of Patent: Feb. 8, 2022

(54) IMAGING FIDUCIAL MARKERS AND METHODS

(71) Applicant: Breast-Med, Inc., Minnetonka, MN (US)

(72) Inventors: Patrick Bolan, Minneapolis, MN (US); Michael G. Garwood, Medina, MN (US); Michael T. Nelson, Golden Valley, MN (US); Daniel A. Halpern, St. Louis Park, MN (US)

(73) Assignee: Breast-Med, Inc., Minnetonka, MN (US)

( * ) Notice: Subject to any disclaimer, the term of this patent is extended or adjusted under 35 U.S.C. 154(b) by 21 days.

(21) Appl. No.: 15/828,021

(22) Filed: Nov. 30, 2017

(65) Prior Publication Data
US 2018/0085184 A1 Mar. 29, 2018

Related U.S. Application Data

(63) Continuation-in-part of application No. 14/966,400, filed on Dec. 11, 2015, now Pat. No. 9,861,450, (Continued)

(51) Int. Cl.
*A61B 90/00* (2016.01)
*A61M 31/00* (2006.01)
(Continued)

(52) U.S. Cl.
CPC ............ *A61B 90/39* (2016.02); *A61B 8/481* (2013.01); *A61B 17/3468* (2013.01);
(Continued)

(58) Field of Classification Search
CPC ..... A61B 8/481; A61B 17/3468; A61B 19/54; A61B 2019/547; A61B 2019/5408;
(Continued)

(56) References Cited

U.S. PATENT DOCUMENTS 2,678,195 A * 5/1954 George ................... E04G 21/08
74/87
5,016,639 A 5/1991 Allen
(Continued)

FOREIGN PATENT DOCUMENTS

| CA | 2579914 A1 | 11/2006 |
|---|---|---|
| CN | 1802125 | 7/2006 |

(Continued)

OTHER PUBLICATIONS

"U.S. Appl. No. 11/281,801, Examiner Interview Summary dated Sep. 2, 2009", 4 pgs.
(Continued)

*Primary Examiner* — Christopher M Koehler
(74) *Attorney, Agent, or Firm* — Schwegman Lundberg & Woessner, P.A.

(57) ABSTRACT

An implantable tissue marker incorporates a contrast agent sealed within a chamber in a container formed from a solid material. The contrast agent is selected to produce a change, such as an increase, in signal intensity under magnetic resonance imaging (MRI). An additional contrast agent may also be sealed within the chamber to provide visibility under another imaging modality, such as computed tomographic (CT) imaging or ultrasound imaging.

21 Claims, 7 Drawing Sheets

Related U.S. Application Data which is a continuation of application No. 14/634,965, filed on Mar. 2, 2015, now Pat. No. 9,241,773, which is a continuation of application No. 14/022,539, filed on Sep. 10, 2013, now Pat. No. 8,966,735, which is a continuation of application No. 12/762,837, filed on Apr. 19, 2010, now Pat. No. 8,544,162, which is a continuation-in-part of application No. 11/281,801, filed on Nov. 17, 2005, now Pat. No. 7,702,378.

(51) Int. Cl.

| | | |
|---|---|---|
| *G01R 33/48* | (2006.01) | |
| *G01R 33/56* | (2006.01) | |
| *A61K 49/22* | (2006.01) | |
| *A61B 17/34* | (2006.01) | |
| *A61B 8/08* | (2006.01) | |
| *A61K 49/18* | (2006.01) | |
| *A61K 49/04* | (2006.01) | |
| *A61K 49/00* | (2006.01) | |
| *G01R 33/58* | (2006.01) | |
| *H01F 41/02* | (2006.01) | |
| *A61M 37/00* | (2006.01) | |

(52) U.S. Cl.
CPC ...... *A61K 49/0002* (2013.01); *A61K 49/0447* (2013.01); *A61K 49/18* (2013.01); *A61K 49/223* (2013.01); *A61M 31/002* (2013.01); *A61M 31/005* (2013.01); *G01R 33/4812* (2013.01); *G01R 33/4814* (2013.01); *G01R 33/5601* (2013.01); *G01R 33/58* (2013.01); *A61B 2090/397* (2016.02); *A61B 2090/3908* (2016.02); *A61B 2090/3925* (2016.02); *A61B 2090/3933* (2016.02); *A61B 2090/3954* (2016.02); *A61B 2090/3958* (2016.02); *A61B 2090/3966* (2016.02); *A61B 2090/3995* (2016.02); *A61M 37/00* (2013.01); *H01F 41/02* (2013.01); *H01F 41/0253* (2013.01); *Y10T 29/49075* (2015.01); *Y10T 29/4998* (2015.01); *Y10T 29/49888* (2015.01); *Y10T 29/49982* (2015.01)

(58) Field of Classification Search
CPC .... A61B 2019/5425; A61B 2019/5454; A61B 2019/5495; A61B 2019/5458; A61B 2019/5466; A61M 31/005; A61K 49/0002; A61K 49/0447; A61K 49/18; A61K 49/226; G01R 33/4814; G01R 33/5601; Y10T 29/4998; Y10T 29/49982; Y10T 29/49888

See application file for complete search history.

(56) References Cited

U.S. PATENT DOCUMENTS

| | | | |
|---|---|---|---|
| 5,097,839 A | 3/1992 | Allen | |
| 5,119,817 A | 6/1992 | Allen | |
| 5,179,955 A | 1/1993 | Leveen et al. | |
| 5,211,164 A | 5/1993 | Allen | |
| 5,394,457 A * | 2/1995 | Leibinger | A61B 6/12 378/162 |
| 5,397,329 A * | 3/1995 | Allen | A61B 6/12 378/205 |
| 5,405,402 A | 4/1995 | Dye et al. | |
| 5,469,847 A | 11/1995 | Zinreich et al. | |
| 5,609,850 A | 3/1997 | Deutsch et al. | |
| 5,702,128 A | 12/1997 | Maxim et al. | |
| 5,769,861 A | 6/1998 | Vilsmeier | |
| 5,782,764 A | 7/1998 | Werne | |
| 6,128,522 A | 10/2000 | Acker et al. | |
| 6,161,034 A | 12/2000 | Burbank et al. | |
| 6,181,960 B1 | 1/2001 | Jensen et al. | |
| 6,269,148 B1 | 7/2001 | Jessop et al. | |
| 6,270,464 B1 | 8/2001 | Fulton, III et al. | |
| 6,333,971 B2 | 12/2001 | McCrory et al. | |
| 6,347,241 B2 | 2/2002 | Burbank et al. | |
| 6,350,244 B1 | 2/2002 | Fisher | |
| 6,356,782 B1 | 3/2002 | Sirimanne et al. | |
| 6,371,904 B1 | 4/2002 | Sirimanne et al. | |
| 6,374,132 B1 | 4/2002 | Acker et al. | |
| 6,394,965 B1 | 5/2002 | Klein | |
| 6,405,072 B1 | 6/2002 | Cosman | |
| 6,419,680 B1 * | 7/2002 | Cosman | G06T 3/4061 378/162 |
| 6,427,081 B1 | 7/2002 | Burbank et al. | |
| 6,487,438 B1 | 11/2002 | Widmark et al. | |
| 6,516,211 B1 | 2/2003 | Acker et al. | |
| 6,544,185 B2 | 4/2003 | Montegrande | |
| 6,546,279 B1 | 4/2003 | Bova et al. | |
| 6,549,802 B2 | 4/2003 | Thornton | |
| 6,567,689 B2 | 5/2003 | Burbank et al. | |
| 6,575,991 B1 | 6/2003 | Chesbrough et al. | |
| 6,605,047 B2 | 8/2003 | Zarins et al. | |
| 6,632,176 B2 | 10/2003 | McIntire et al. | |
| 6,635,064 B2 | 10/2003 | U et al. | |
| 6,656,192 B2 | 12/2003 | Espositio et al. | |
| 6,662,041 B2 | 12/2003 | Burbank et al. | |
| 6,699,205 B2 | 3/2004 | Fulton, III et al. | |
| 6,725,083 B1 | 4/2004 | Burbank et al. | |
| 6,730,042 B2 | 5/2004 | Fulton et al. | |
| 6,746,661 B2 | 6/2004 | Kaplan | |
| 6,761,679 B2 | 7/2004 | Sajo et al. | |
| 6,773,408 B1 | 8/2004 | Acker et al. | |
| 6,778,850 B1 | 8/2004 | Adler et al. | |
| 6,862,470 B2 | 3/2005 | Burbank et al. | |
| 6,927,406 B2 | 8/2005 | Zyromski | |
| 6,993,375 B2 | 1/2006 | Burbank et al. | |
| 6,996,433 B2 | 2/2006 | Burbank et al. | |
| 7,010,340 B2 | 3/2006 | Scarantino et al. | |
| 7,044,957 B2 | 5/2006 | Foerster et al. | |
| 7,047,063 B2 | 5/2006 | Burbank et al. | |
| 7,226,442 B2 | 6/2007 | Sheppard, Jr. et al. | |
| 7,668,582 B2 | 2/2010 | Sirimanne et al. | |
| 7,702,378 B2 | 4/2010 | Bolan et al. | |
| 7,792,568 B2 | 9/2010 | Zhong et al. | |
| 8,280,486 B2 | 10/2012 | Miller et al. | |
| 8,544,162 B2 | 10/2013 | Bolan et al. | |
| 8,966,735 B2 | 3/2015 | Bolan et al. | |
| 9,241,773 B2 | 1/2016 | Bolan et al. | |
| 9,795,455 B2 | 10/2017 | Bolan et al. | |
| 9,861,450 B2 | 1/2018 | Bolan et al. | |
| 2002/0035324 A1 | 3/2002 | Sirimanne et al. | |
| 2002/0083591 A1 | 7/2002 | Geertsma et al. | |
| 2002/0083951 A1 * | 7/2002 | Stegmaier | A61B 90/90 128/899 |
| 2002/0107437 A1 | 8/2002 | Sirimanne et al. | |
| 2002/0161298 A1 | 10/2002 | Burbank et al. | |
| 2002/0188196 A1 | 12/2002 | Burbank et al. | |
| 2003/0023161 A1 | 1/2003 | Govari et al. | |
| 2004/0030262 A1 * | 2/2004 | Fisher | A61L 24/0015 600/564 |
| 2004/0176684 A1 * | 9/2004 | Tabuchi | A61B 1/041 600/424 |
| 2004/0186377 A1 * | 9/2004 | Zhong | A61M 25/00 600/431 |
| 2004/0193044 A1 | 9/2004 | Burbank et al. | |
| 2004/0236211 A1 | 11/2004 | Burbank et al. | |
| 2004/0236212 A1 | 11/2004 | Jones et al. | |
| 2004/0236213 A1 | 11/2004 | Jones et al. | |
| 2005/0004456 A1 | 1/2005 | Thomas et al. | |
| 2005/0020916 A1 | 1/2005 | MacFarlane et al. | |
| 2005/0033157 A1 | 2/2005 | Klein et al. | |
| 2005/0035324 A1 | 2/2005 | McPeak et al. | |
| 2005/0059884 A1 | 3/2005 | Kragg | |
| 2005/0059888 A1 | 3/2005 | Sirimanne et al. | |
| 2005/0065393 A1 | 3/2005 | Miller | |
| 2005/0080337 A1 | 4/2005 | Sirimanne et al. | |
| 2005/0080338 A1 | 4/2005 | Sirimanne et al. | |

(56) References Cited

U.S. PATENT DOCUMENTS

| | | | |
|---|---|---|---|
| 2005/0080339 A1 | 4/2005 | Sirimanne et al. | |
| 2005/0085724 A1 | 4/2005 | Sirimanne et al. | |
| 2005/0143656 A1 | 6/2005 | Burbank et al. | |
| 2005/0154293 A1* | 7/2005 | Gisselberg | A61B 5/06 600/420 |
| 2005/0205445 A1 | 9/2005 | Seiler et al. | |
| 2005/0234336 A1 | 10/2005 | Beckman et al. | |
| 2005/0255045 A1 | 11/2005 | Woltering | |
| 2006/0036165 A1 | 2/2006 | Burbank et al. | |
| 2006/0058645 A1 | 3/2006 | Komistek et al. | |
| 2006/0058648 A1 | 3/2006 | Meier et al. | |
| 2006/0079805 A1 | 4/2006 | Miller et al. | |
| 2006/0084865 A1 | 4/2006 | Burbank et al. | |
| 2006/0122503 A1 | 6/2006 | Burbank et al. | |
| 2006/0155190 A1 | 7/2006 | Brubank et al. | |
| 2006/0173296 A1 | 8/2006 | Miller et al. | |
| 2006/0293581 A1 | 12/2006 | Plewes et al. | |
| 2007/0087026 A1 | 4/2007 | Filed | |
| 2007/0093726 A1 | 4/2007 | Leopold et al. | |
| 2007/0110665 A1 | 5/2007 | Bolan et al. | |
| 2007/0118034 A1 | 5/2007 | Mark | |
| 2007/0142725 A1 | 7/2007 | Hardin et al. | |
| 2007/0238984 A1* | 10/2007 | Maschke | A61B 5/0031 600/424 |
| 2008/0033286 A1 | 2/2008 | Whitmore et al. | |
| 2008/0234572 A1 | 9/2008 | Jones | |
| 2008/0269603 A1 | 10/2008 | Nicoson et al. | |
| 2009/0069670 A1 | 3/2009 | Mark | |
| 2009/0105584 A1 | 4/2009 | Jones | |
| 2009/0213997 A1 | 8/2009 | Maschke | |
| 2010/0030072 A1* | 2/2010 | Casanova | A61B 6/481 600/431 |
| 2010/0121225 A1 | 5/2010 | Lewkowicz et al. | |
| 2010/0287887 A1 | 11/2010 | Bolan et al. | |
| 2011/0184279 A1* | 7/2011 | Massonneau | A61B 1/041 600/431 |
| 2011/0276070 A1 | 11/2011 | Viray et al. | |
| 2013/0046164 A1 | 2/2013 | Liu et al. | |
| 2013/0150707 A1 | 6/2013 | Cima et al. | |
| 2013/0324946 A1 | 12/2013 | Tobias et al. | |
| 2014/0187911 A1 | 7/2014 | Bolan et al. | |
| 2015/0173848 A1 | 6/2015 | Bolan et al. | |
| 2016/0051337 A1 | 2/2016 | Bolan et al. | |
| 2016/0010091 A1 | 4/2016 | Bolan et al. | |

FOREIGN PATENT DOCUMENTS

| | | |
|---|---|---|
| CN | 102056544 | 5/2011 |
| CN | 107205792 A | 9/2017 |
| CN | 107205792 | 6/2020 |
| EP | 1491147 A1 | 12/2004 |
| EP | 1579878 A1 | 9/2005 |
| EP | 1847845 A1 | 10/2007 |
| EP | 3182919 | 10/2018 |
| TW | 201143798 | 12/2011 |
| WO | WO-9717103 A1 | 5/1997 |
| WO | WO-0024332 A1 | 5/2000 |
| WO | WO-0038579 A2 | 7/2000 |
| WO | WO-0230482 A1 | 4/2002 |
| WO | WO-03022133 A2 | 3/2003 |
| WO | WO-03051452 A1 | 6/2003 |
| WO | WO-2004084738 A1 | 10/2004 |
| WO | WO-2005046733 A1 | 5/2005 |
| WO | WO-2005063126 A2 | 7/2005 |
| WO | WO-06044132 A1 | 4/2006 |
| WO | WO-2006119645 A1 | 11/2006 |
| WO | WO-2007060576 A2 | 5/2007 |
| WO | 2012040455 | 3/2012 |
| WO | WO-2016028976 A1 | 2/2016 |
| WO | WO-2016028976 A8 | 2/2016 |

OTHER PUBLICATIONS

"U.S. Appl. No. 11/281,801, Final Office Action dated Mar. 13, 2009", 18 pgs.

"U.S. Appl. No. 11/281,801, Non-Final Office Action dated Sep. 22, 2008", 12 pgs.

"U.S. Appl. No. 11/281,801, Notice of Allowance dated Dec. 2, 2009", 10 pgs.

"U.S. Appl. No. 11/281,801, Response filed Dec. 18, 2008 to Non-Final Office Action dated Sep. 22, 2008", 25 pgs.

"U.S. Appl. No. 11/281,801, Response filed Jun. 12, 2009 to Final Office Action dated Mar. 13, 2009", 27 pgs.

"U.S. Appl. No. 11/281,801, Response filed Jul. 17, 2008 to Restriction Requirement dated Apr. 17, 2008", 13 pgs.

"U.S. Appl. No. 11/281,801, Restriction Requirement dated Apr. 17, 2008", 5 pgs.

"U.S. Appl. No. 11/281,801, Supplemental Response filed Aug. 24, 2009 to Final Office Action dated Mar. 13, 2009", 29 pgs.

"U.S. Appl. No. 11/281,801, Supplemental Response filed Aug. 25, 2009 to Final Office Action dated Mar. 13, 2009", 2 pgs.

"U.S. Appl. No. 11/281,801, Supplemental Response filed Aug. 28, 2009 to Final Office Action dated Mar. 13, 2009", 16 pgs.

"U.S. Appl. No. 12/762,837, Non Final Office Action dated Nov. 2, 2012", 15 pgs.

"U.S. Appl. No. 12/762,837, Notice of Allowance dated May 30, 2013", 6 pgs.

"U.S. Appl. No. 12/762,837, Response filed Jan. 18, 2013 to Non Final Office Action dated Nov. 2, 2012", 14 pgs.

"U.S. Appl. No. 14/022,539, Final Office Action dated Jul. 24, 2014", 7 pgs.

"U.S. Appl. No. 14/022,539, Non Final Office Action dated Apr. 11, 2014", 8 pgs.

"U.S. Appl. No. 14/022,539, Notice of Allowance dated Oct. 24, 2014", 10 pgs.

"U.S. Appl. No. 14/022,539, Preliminary Amendment filed Mar. 10, 2014", 8 pgs.

"U.S. Appl. No. 14/022,539, Response filed Jul. 11, 2014 to Non Final Office Action dated Apr. 11, 2014", 10 pgs.

"U.S. Appl. No. 14/466,010, Advisory Action dated May 15, 2017", 3 pgs.

"U.S. Appl. No. 14/466,010, Final Office Action dated Dec. 30, 2016", 8 pgs.

"U.S. Appl. No. 14/466,010, Non Final Office Action dated Sep. 8, 2016", 7 pgs.

"U.S. Appl. No. 14/466,010, Notice of Allowance dated Jun. 21, 2017", 7 pgs.

"U.S. Appl. No. 14/466,010, Response filed May 1, 2017 to Final Office Action dated Dec. 30, 2016", 12 pgs.

"U.S. Appl. No. 14/466,010, Response filed Dec. 1, 2016 to Non Final Office Action dated Sep. 8, 2016", 12 pgs.

"U.S. Appl. No. 14/634,965, Non Final Office Action dated May 20, 2015", 10 pgs.

"U.S. Appl. No. 14/634,965, Notice of Allowance dated Sep. 15, 2015", 10 pgs.

"U.S. Appl. No. 14/634,965, Preliminary Amendment filed Mar. 3, 2015", 9 pgs.

"U.S. Appl. No. 14/634,965, Response filed Apr. 28, 2015 to Restriction Requirement filed Apr. 8, 2015", 9 pgs.

"U.S. Appl. No. 14/634,965, Response filed Aug. 18, 2015 to Non Final Office Action dated May 20, 2015", 12 pgs.

"U.S. Appl. No. 14/634,965, Restriction Requirement dated Apr. 8, 2015", 7 pgs.

"U.S. Appl. No. 14/966,400, Non Final Office Action dated May 2, 2017", 10 pgs.

"U.S. Appl. No. 14/966,400, Notice of Allowance dated Aug. 30, 2017", 5 pgs.

"U.S. Appl. No. 14/966,400, Preliminary Amendment filed Dec. 15, 2015", 6 pgs.

"U.S. Appl. No. 14/966,400, Response filed Apr. 10, 2017 to Restriction Requirement dated Feb. 8, 2017", 7 pgs.

"U.S. Appl. No. 14/966,400, Response filed Aug. 2, 2017 to Non Final Office Action dated May 2, 2017", 9 pgs.

"U.S. Appl. No. 14/966,400, Restriction Requirement dated Feb. 8, 2017", 7 pgs.

(56) References Cited

OTHER PUBLICATIONS

"International Application Serial No. PCT/US2015/046038, International Preliminary Report on Patentability dated Mar. 9, 2017", 9 pgs.

"International Application Serial No. PCT/US2015/046038, International Search Report dated Oct. 21, 2015", 4 pgs.

"International Application Serial No. PCT/US2015/046038, Written Opinion dated Oct. 21, 2015", 7 pgs.

Bolan, P. J., et al., "A Novel Soft Tissue Marker for Multimodal Breast Imagine with Positive MRI Contrast", Joint Annual Meeting ISMRM-ESMRMB, (May 2007), 1 pg.

Bolan, Patrick, "A Novel Tissue Marker for Multimodal Breast Imaging (Abstract)", Abstract submitted Apr. 2005, published Radiological Society of North America (RSNA), Nov. 2005., [Online], Retrieved from the Internet: <URL: http://abstract.rsna.org/index.cfm?fuseaction~submission.popupPrevie . . . >, (Nov. 2005), 2 pgs.

Bolan, Patrick, "Soft Tissue Markers or Clips (Presentation)", This work was supported under NIH grants, the MIND institute, and the Keck Foundation., (Nov. 16, 2005), 16 pgs.

Ellis, R. E., et al., "Use of Biocompatible Fiducial Marker in Evaluating the Accuracy of CT Image Registration", Investigative Radiology, (1996), 1-9.

Frank, Steven J., et al., "A Novel MRI Marker for Prostate Brachytherapy", Int. J. Radiation Oncology Biol. Phys., vol. 70, No. 1, (2008), 5-8.

Gierga, D. P., et al., "The Correlation between Internal and External Markers for Abdominal Tumors: Implications for Respiratory Gating", Int J Radial Oncol Biol Phys.; 61 (f); 1551-8, (Apr. 1, 2005), 1 pg.

Igdem, S., et al., "Implantation of Fiducial Markers for Image Guidance in Prostate Radiotherapy: Patient-reported toxicity", The British Journal of Radiology, (2009), 1-5.

Maier-Hein, L, et al., "On Combining Internal and External Fiducials for Liver Motion Compensation", Comput Aided Surg.; 13(6): 369-76, (Nov. 2008), 1 pg.

"European Application Serial No. 15756323.0, Response filed Oct. 6, 2017 to Communication pursuant to Rules 161(1) and 162 EPC dated Apr. 7, 2017", 17 pgs.

"Chinese Application Serial No. 201580057297.8, Office Action dated Mar. 7, 2019", w English Translation, 12 pgs.

"Chinese Application Serial No. 201580057297.8, Response filed Jan. 19, 2020 to Office Action dated Mar. 7, 2019", with English claims, 11 pages.

"Canadian Application Serial No. 2,958,861, Voluntary Amendment filed Aug. 14, 2020", 10 pages.

"Canadian Application Serial No. 2,958,861, Office Action dated Aug. 27, 2020", 4 pages.

"Canadian Application Serial No. 2,958,861, Response filed Mar. 17, 2021 to Office Action dated Jan. 25, 2021", 12 pgs.

"Canadian Application Serial No. 2,958,861, Office Action dated Jan. 25, 2021", 4 pgs.

"Canadian Application Serial No. 2,958,861, Response filed Dec. 9, 2020 to Office Action dated Aug. 27, 2020", 13 pgs.

"Canadian Application Serial No. 2,958,861, Office Action dated Jul. 22, 2021", 4 pgs.

"Canadian Application Serial No. 2,958,861, Office Action dated Jul. 22, 2021", 3 pgs.

U.S. Appl. No. 11/281,801 U.S. Pat. No. 7,702,378, filed Nov. 17, 2005, Tissue Marker for Multimodality Radiographic Imaging.

U.S. Appl. No. 12/762,837 U.S. Pat. No. 8,544,162, filed Apr. 19, 2010, Tissue Marker for Multimodality Radiographic Imaging.

U.S. Appl. No. 14/022,539 U.S. Pat. No. 8,966,735, filed Sep. 10, 2013, Tissue Marker for Multimodality Radiographic Imaging.

U.S. Appl. No. 14/634,965 U.S. Pat. No. 9,241,773, filed Mar. 2, 2015, Imaging Fiducial Markers and Methods.

U.S. Appl. No. 14/966,400, filed Dec. 11, 2015, Imaging Fiducial Markers and Methods.

U.S. Appl. No. 14/466,010 U.S. Pat. No. 9,795,455, filed Aug. 22, 2014, Tissue Marker for Multimodality Radiographic Imaging.

"Canadian Application Serial No. 2,958,861, Response filed Oct. 6, 2021 Office Action dated Jul. 22, 2021", 18 pgs.

"Canadian Application 2,958,861 Commissioner's Notice— Application Found Allowable Nov. 17, 2017", (Nov. 17, 2021), 1 page.

* cited by examiner

IMAGING FIDUCIAL MARKERS AND METHODS

CLAIM OF PRIORITY

This application is a continuation-in-part of U.S. patent application Ser. No. 14/966,400, filed Dec. 11, 2015, which is a continuation of U.S. patent application Ser. No. 14/634,965, filed Mar. 2, 2015, which is a continuation of Ser. No. 14/022,539, filed on Sep. 10, 2013, which is a continuation of U.S. Ser. No. 12/762,837, filed on Apr. 19, 2010, which is a continuation-in-Part of U.S. application Ser. No. 11/281,801, filed Nov. 17, 2005, and issued as U.S. Pat. No. 7,702,378 on Apr. 20, 2010, all of which are incorporated herein by reference in their entireties and the benefit of priority of each of which is claimed herein.

TECHNICAL FIELD

The disclosure relates generally to tissue markers. More particularly, the disclosure relates to implantable tissue markers for use in magnetic resonance imaging.

BACKGROUND

Certain medical conditions, including breast cancer, are increasingly being diagnosed and treated using minimally invasive medical techniques. Such techniques typically involve the use of clinical imaging methods that allow the physician to visualize interior portions of a patient's body without the need to make excessive incisions or cause avoidable collateral damage to healthy adjacent tissue. Imaging can be performed using any of variety of modalities, including, for example, X-rays, computed tomographic (CT) X-ray imaging, fluoroscopy, portal film imaging devices, electronic portal imaging devices, ultrasound, electrical impedance tomography (EIT), magnetic resonance (MR) imaging, or MRI, magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), brain electrical activity mapping (BEAM), arterial contrast injection angiography, and digital subtraction angiography. Nuclear medicine modalities include positron emission tomography (PET) and single photon emission computed tomography (SPECT).

Some of these imaging procedures involve the use of radiographic markers. Radiographic markers are small devices that are implanted in a patient during surgical procedures, such as biopsies. Conventional markers typically consist of one or more solid objects, such as a piece of metallic wire, ceramic beads, etc., which are implanted either by themselves or within a gelatinous matrix, collagen, or polylactic acid, to temporarily increase visibility, for example, to ultrasound imaging. They are designed to be visible to one of the imaging modalities listed above and typically have a shape that is readily identifiable as an artificial structure, as contrasted from naturally occurring anatomical structures in the patient's body. For example, markers can be shaped as coils, stars, rectangles, spheres, or other shapes that do not occur in anatomical structures. Such markers enable radiologists to localize the site of surgery in subsequent imaging studies or to facilitate image registration during image-guided therapeutic procedures. In this way, markers can serve as landmarks that provide a frame of reference for the radiologist.

Most conventional markers appear as a signal void, i.e., a dark artifact, in magnetic resonance imaging. This manifestation can be particularly problematic in some contexts. For example, heterogeneous breast tissue produces many dark artifacts under MR imaging, thereby rendering small signal voids produced by some conventional markers difficult to identify and distinguish from naturally occurring dark artifacts. In addition, some markers produce large susceptibility artifacts under MR imaging, thereby distorting images in both MRI and spectroscopic modalities. Some markers incorporate an external gel that may produce a positive or bright signal, but such gels are not permanent. Some other markers contain collagen or polylactic acid, which may interfere with magnetic resonance spectroscopy. With the increasing use of MR imaging techniques in the treatment of breast cancer in clinical settings, improved MR visibility of tissue markers is particularly desirable.

OVERVIEW

According to various example embodiments, an implantable tissue marker incorporates a contrast agent sealed within a chamber in a container formed from a solid material. The contrast agent is selected to produce a change in signal intensity under magnetic resonance imaging (MRI). An additional contrast agent may also be sealed within the chamber to provide visibility under another imaging modality, such as computed tomographic (CT) imaging or ultrasound imaging.

One embodiment is directed to a permanently implantable radiographic marker. A container formed from a solid material defines an internal chamber, in which a contrast agent is sealed. The contrast agent is selected to produce an increase in signal intensity in a magnetic resonance (MR) imaging modality. Another embodiment is directed to a method of manufacturing such a marker.

In another embodiment, a permanently implantable fiducial marker includes a container formed from a nonbiodegradable solid material. The container defines an internal chamber. A first contrast agent is sealed within the internal chamber and is selected to produce an increase in signal intensity in a magnetic resonance (MR) imaging modality. A second contrast agent sealed within the internal chamber. The second contrast agent is selected to produce a signal in another imaging modality.

Another embodiment is directed to a method of identifying a location within a body of a patient. A marker is implanted proximate the location. The marker comprises a container formed from a solid material and defining an internal chamber, and a contrast agent sealed within the internal chamber. The contrast agent is selected to produce an increase in signal intensity in a magnetic resonance (MR) imaging modality. A first image of the location is generated in the magnetic resonance (MR) imaging modality.

Various embodiments may provide certain advantages. For instance, a contrast agent selected to produce an increase in signal intensity in an MR imaging modality may produce good visualization characteristics without also producing an excessive artifact and without interfering with MR spectroscopy or diffusion imaging. Production of an increase in signal intensity in an MR imaging modality may be particularly beneficial in certain contexts, such as, for example, imaging of breast tissue, which is heterogeneous.

Additional objects, advantages, and features will become apparent from the following description and the claims that follow, considered in conjunction with the accompanying drawings.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

According to various embodiments, an implantable tissue marker incorporates a contrast agent sealed within a chamber in a container formed from a solid material. The contrast agent is selected to produce an increase in signal intensity under magnetic resonance imaging (MRI). An additional contrast agent may also be sealed within the chamber to provide visibility under another imaging modality, such as computed tomographic (CT) imaging or ultrasound imaging.

In this way, certain advantages may be realized. For instance, a contrast agent selected to produce an increase in signal intensity in an MR imaging modality may produce good visualization characteristics without also producing an excessive artifact and without interfering with MR spectroscopy or diffusion imaging. Producing an increase in signal intensity in an MR imaging modality may be particularly beneficial in certain contexts, such as, for example, imaging of breast tissue. Most conventional markers appear as a signal void in MR imaging. The heterogeneous nature of breast tissue makes small signal voids difficult to identify. By producing an increase in signal intensity, i.e., a bright area, in MR imaging, the implantable tissue markers disclosed herein may be easier to see than conventional markers.

The following description of various embodiments implemented in the context of imaging certain types of tissue is to be construed by way of illustration rather than limitation. This description is not intended to limit the invention or its applications or uses. For example, while various embodiments are described as being implemented in the context of imaging breast tissue, it will be appreciated that the principles of the disclosure are applicable to other contexts, such as image registration during image guided therapeutic procedures. In further examples, while various embodiments are described as being implemented in the context of imaging breast tissue, it will be appreciated that the principles of the disclosure are applicable to other anatomical sites, such as prostate, brain, spinal, and other anatomical sites.

In the following description, numerous specific details are set forth in order to provide a thorough understanding of various embodiments. It will be apparent to one skilled in the art that some embodiments may be practiced without some or all of these specific details. In other instances, well known components and process steps have not been described in detail.

Figure 1:
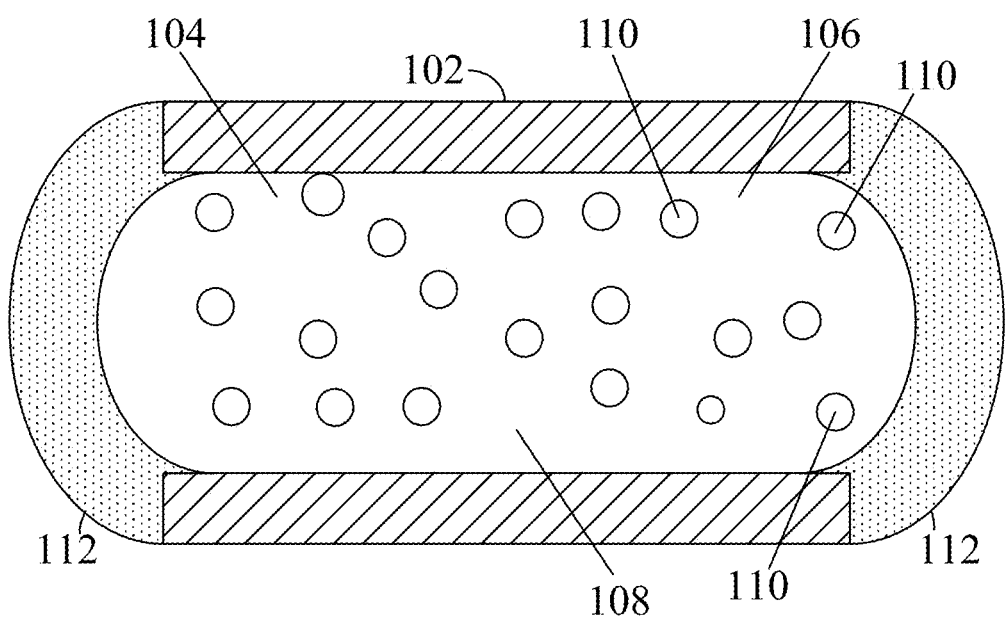
FIG. 1 is a sectional view of a tissue marker according to one embodiment.

Referring now to the drawings, FIG. 1 is a sectional view illustrating an example implantable radiographic marker 100 according to one embodiment. A tube 102 is formed from a nonbiodegradable radiopaque solid material, such as glass, plastic, carbon fiber, or silicone. For example, the tube 102 may be formed from LEXAN® polycarbonate resin, commercially available from General Electric Company, headquartered in Pittsfield, Mass. The tube 102 is preferably sized for insertion via a biopsy cannula. For example, in one particular implementation, the tube 102 has a major dimension of approximately 3-4 mm and a minor dimension of approximately 1-2 mm.

The tube 102 defines two end portions 104 and 106, at least one of which is initially open. A chamber 108 is defined within the tube 102 between the two end portions 104 and 106. One or more contrast agents 110 are introduced into the chamber 108. The end portions 104 and 106 are then sealed, for example, using a sealant 112 such as epoxy. In some embodiments, a permanent biocompatible adhesive such as cyanoacrylate serves as the sealant 112.

The visual representation of the contrast agents 110 in FIG. 1 is intended only to distinguish the contrast agents 110 from the chamber 108 in which they are disposed. According to various embodiments, the contrast agents 110 can be implemented as a gas, gel, or liquid, or as a combination of gases, gels, and/or liquids. Each of these materials can be selected independently to customize the appearance of the marker 100 in different imaging modalities and under different conditions, e.g., with or without contrast, and in various tissue types.

For instance, if the marker 100 is to be visible in magnetic resonance (MR) and computed tomography (CT) imaging modalities, the chamber 108 may contain a mixture of a gadolinium-DTPA MR contrast agent and an iodinated CT contrast agent. The volume of contrast agent 110 in the chamber 108 may be maximized to promote visibility. Visibility is also promoted by matching the magnetic susceptibility of the contrast agent 110 and the magnetic susceptibility of the tube 102. If it is further desired that the marker 100 be visible in an ultrasound imaging modality, the chamber 108 may also contain a gas bubble.

In some embodiments, the tube 102 itself, rather than multiple contrast agents 110, may provide visibility in certain imaging modalities. For example, the tube 102 may be made of a radiopaque polymer that provides contrast in X-ray imaging modalities. As another example, a difference in acoustic impedance between the tube 102 and the material in the chamber 108 will cause the marker 100 to reflect ultrasound waves, thereby promoting visibility in an ultrasound imaging modality. Further, if the magnetic susceptibility of the tube 102 is similar to that of the material in the chamber 108 and to that of the surrounding tissue, visibility in MR imaging modalities will be improved due to improved magnetic field homogeneity and reduced T2*artifact.

In one particular embodiment, the marker 100 is formed by cutting a glass micropipette, commercially available from Fisher Scientific, headquartered in Hampton, N.H., to the desired length, e.g., 4 mm, to form the tube 102. The micropipette has an outer diameter appropriate for insertion via a biopsy cannula, e.g., 2 mm.

Contrast agents 110 are then introduced into the chamber 108 defined by the tube 102. In one particular embodiment, for example, an MR contrast agent and a CT contrast agent are combined, and the liquid mixture resulting from this combination is injected into the micropipette via a syringe of appropriate gauge, e.g., 25 ga. The MR contrast agent may be implemented as a gadolinium-based MR contrast agent, such as MAGNEVIST® MR contrast agent, commercially available from Berlex, headquartered in Montville, N.J. Other MR contrast agents include, but are not limited to, OMNISCAN™ MR contrast agent, commercially available from GE Healthcare, headquartered in Chalfont St. Giles, United Kingdom, PROHANCE® MR contrast agent, and OPTIMARK® MR contrast agent, commercially available from Tyco Healthcare/Mallinckrodt, Inc., headquartered in St. Louis, Mo. The CT contrast agent may be implemented as an iodinated CT contrast agent, such as OMNIPAQUE™ CT contrast agent, commercially available from GE Healthcare, headquartered in Chalfont St. Giles, United Kingdom. Other CT contrast agents include, but are not limited to, HEXABRIX®, TELEBRIX®, and CONRAY® CT contrast agents, commercially available from Tyco Healthcare/Mallinckrodt, Inc., headquartered in St. Louis, Mo. After the mixture is injected in the chamber 108, the ends of the tube 102 are sealed using a quick-setting epoxy.

Markers 100 of the type illustrated in FIG. 1 and described above have been evaluated for visibility in multiple imaging modalities. Markers 100 were made according to the above-described procedure and were suspended in a gelatin phantom. Magnetic resonance imaging (MRI) was performed on the gelatin phantom using a Siemens Trio 3T (3 Tesla) human MRI scanner. The MRI process used T1-weighted 3D fast low angle shot (FLASH) images, which are typical for MR examinations of breast tissue. In addition, the gelatin phantom was also imaged using a clinical breast X-ray mammography system and a breast ultrasound using standard settings.

Figure 4:
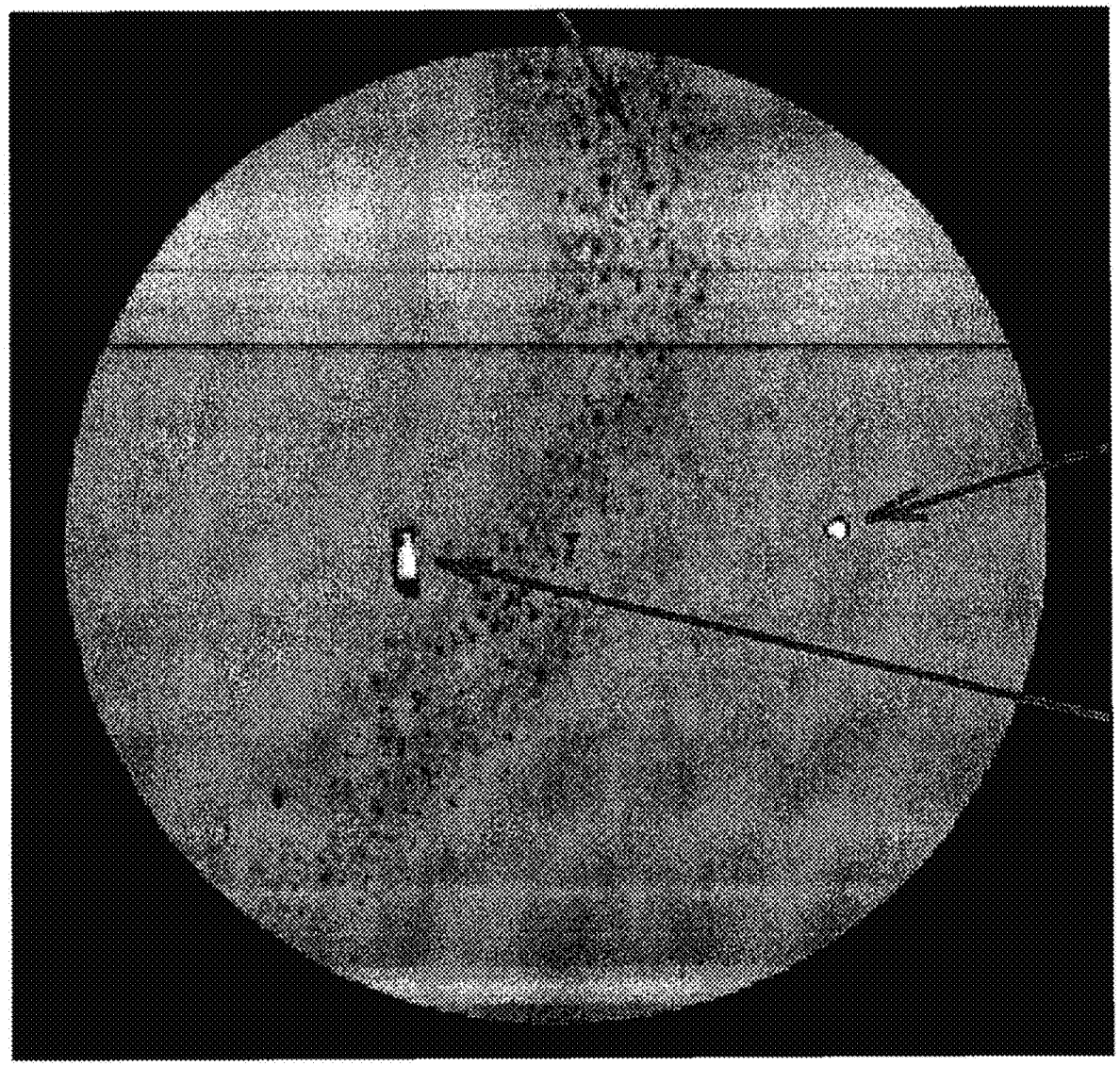
FIG. 4 is an image of the tissue marker of FIG. 1 as visible in a magnetic resonance imaging (MRI) modality.
Figure 5:
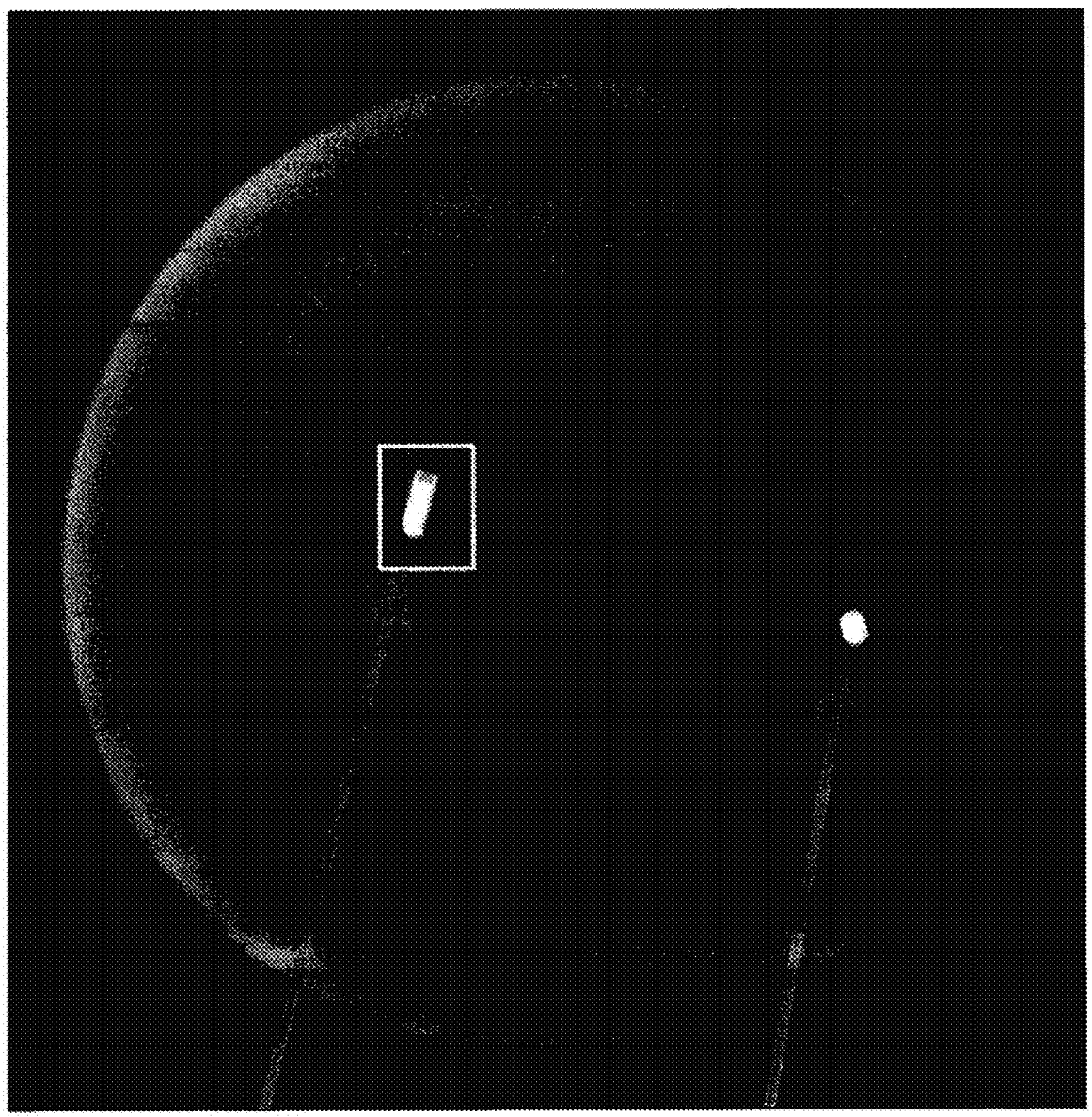
FIG. 5 is an image of the tissue marker of FIG. 1 as visible in an x-ray mammography modality.
Figure 6:
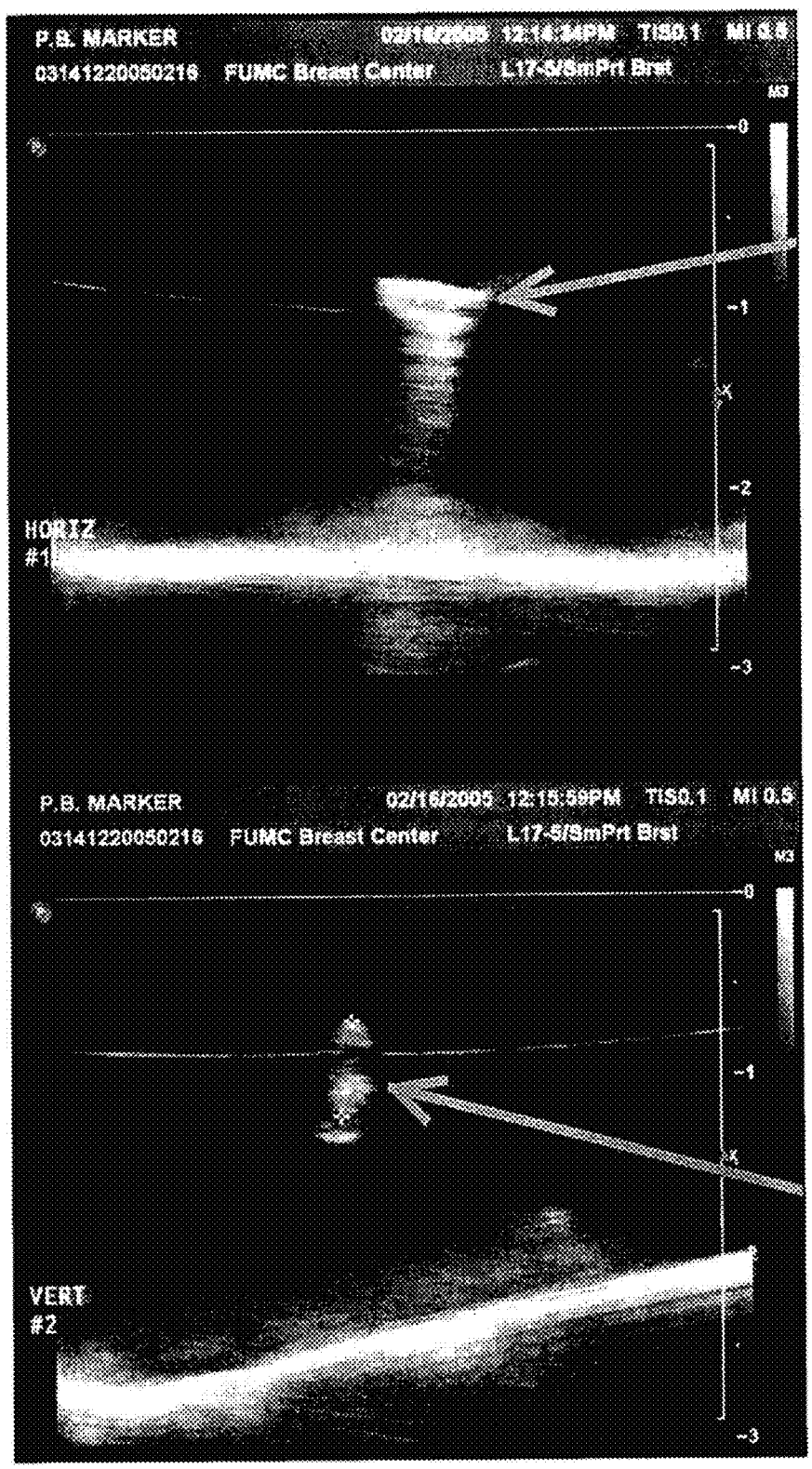
FIG. 6 is an image of the tissue marker of FIG. 1 as visible in an ultrasound imaging modality.

The evaluation of the markers 100 demonstrated that the markers 100 were clearly visible on the three modalities, namely, MRI, X-ray mammography, and ultrasound. FIGS. 4-6 are images of markers 100 obtained under the MRI, X-ray mammography, and ultrasound modalities, respectively. The markers 100 appeared as small signal voids, i.e., dark spots, under low-resolution MRI (0.8 mm in plane). However, the contrast agent 110 in the chamber 108 appeared hyperintense, that is, as bright spots, under higher MRI resolutions, e.g., 0.4 mm in plane. Accordingly, using higher MRI resolutions, the markers 100 are more clearly distinguishable from surrounding tissue than conventional markers that appear as signal voids. The bright signal seen at higher MRI resolutions may be particularly advantageous in imaging heterogeneous breast tissue, in which signal voids may be difficult to see.

In addition to the MRI modality, the markers 100 were also visible in the X-ray mammography and ultrasound imaging modalities. In the X-ray mammography modality, the radiopaque liquid occupying the chamber 108 could be seen clearly with distinct edges. In the ultrasound modality, the tube 102 appeared hyperechoic, while the contrast agents 110 occupying the chamber 108 appeared dark. In this modality, the markers 100 were most easily seen when they were oriented parallel to the transducer surface. However, the markers 100 could also be detected when they were oriented perpendicular to the transducer surface.

According to various embodiments, the contrast agents 110 that are sealed within the chamber 108 can be selected for visibility in any of a number of imaging modalities. Besides the MR, X-ray, and ultrasound imaging modalities mentioned above, contrast agents can be selected for visibility in computed tomographic (CT) X-ray imaging, fluoroscopy, portal film imaging, electronic portal imaging, electrical impedance tomography (EIT), magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), brain electrical activity mapping (BEAM), arterial contrast injection angiography, and digital subtraction angiography modalities. Nuclear medicine modalities include positron emission tomography (PET) and single photon emission computed tomography (SPECT). In addition, as additional imaging modalities are developed in the future, it will be possible to seal contrast agents within the chamber 108 that are selected for visibility in such future modalities.

Figure 2:
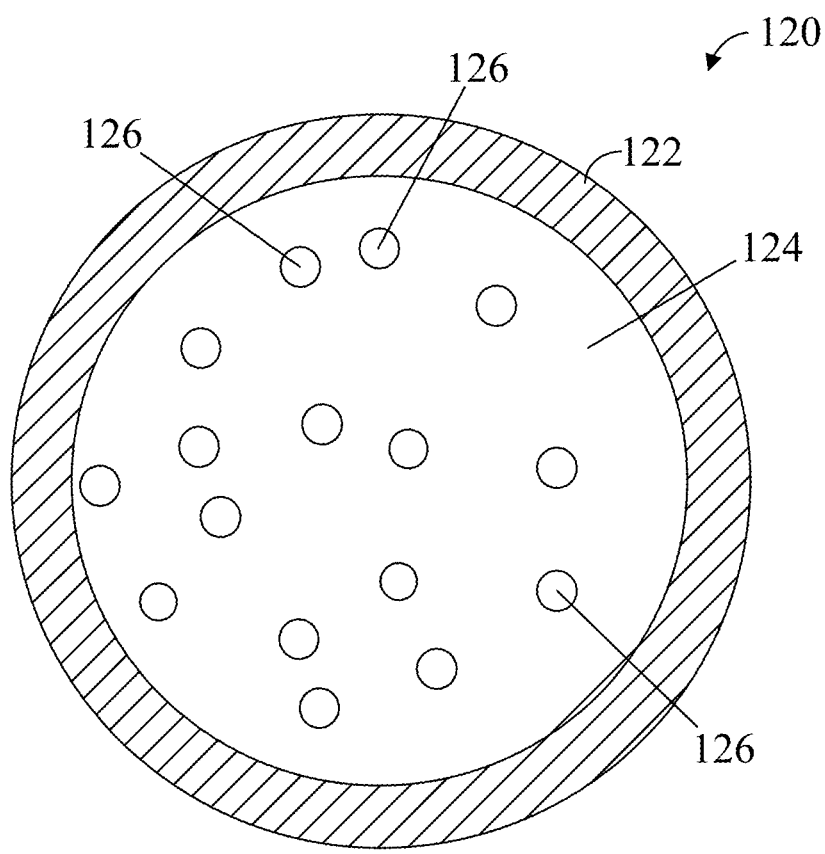
FIG. 2 is a sectional view of a tissue marker according to another embodiment.

FIG. 2 is a sectional view of another example tissue marker 120 according to another embodiment. The tissue marker 120 incorporates an outer capsule 122 formed from a nonbiodegradable radiopaque solid material, such as silicone. The capsule 122 is generally spherical in shape and is preferably sized for insertion via a biopsy cannula. The capsule 122 defines an internal chamber 124.

One or more contrast agents 126 are introduced into the chamber 124, for example, by injecting the contrast agents 126 into the chamber 124. The visual representation of the contrast agents 126 in FIG. 2 is intended only to distinguish the contrast agents 126 from the chamber 124 in which they are disposed. According to various embodiments, the contrast agents 126 can be implemented as a gas, gel, or liquid, or as a combination of gases, gels, and/or liquids. Each of these materials can be selected independently to customize the appearance of the marker 120 in different imaging modalities and under different conditions, e.g., with or without contrast, and in various tissue types. For instance, if the marker 120 is to be visible in magnetic resonance (MR) and computed tomographic (CT) imaging modalities, the chamber 124 may contain a mixture of a gadolinium-DTPA MR contrast agent, such as MAGNEVIST® MR contrast agent, and an iodinated CT contrast agent, such as OMINIPAQUE™ CT contrast agent. The volume of contrast agent 126 in the chamber 124 may be maximized to promote visibility. Visibility is also promoted by matching the magnetic susceptibility of the contrast agent 126 and the magnetic susceptibility of the capsule 122. If it is further desired that the marker 120 be visible in an ultrasound imaging modality, the chamber 124 may also contain an air bubble. After the mixture is injected in the chamber 124, the capsule 122 is sealed.

In some embodiments, the capsule 122 itself, rather than multiple contrast agents 126, may provide visibility in certain imaging modalities. For example, the capsule 122 may be made of a radiopaque polymer that provides contrast in X-ray imaging modalities. As another example, a difference in acoustic impedance between the capsule 122 and the material in the chamber 124 will cause the marker 120 to reflect ultrasound waves, thereby promoting visibility in an ultrasound imaging modality. Further, if the magnetic susceptibility of the capsule 122 is similar to that of the material in the chamber 124 and to that of the surrounding tissue, visibility in MR imaging modalities will be improved due to reduction of T2 darkening.

Figure 3:
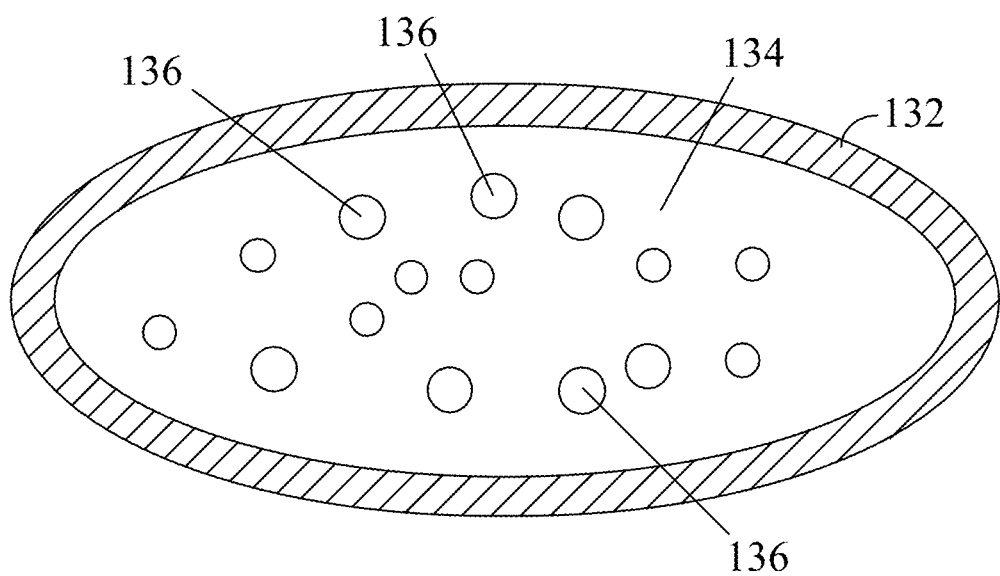
FIG. 3 is a sectional view of a tissue marker according to yet another embodiment.

FIG. 3 is a sectional view of another example tissue marker 130 according to another embodiment. The tissue marker 130 incorporates an outer capsule 132 formed from a nonbiodegradable radiopaque solid material, such as silicone. The capsule 132 is generally spheroid in shape and is preferably sized for insertion via a biopsy cannula. The capsule 132 defines an internal chamber 134.

One or more contrast agents 136 are introduced into the chamber 134, for example, by injecting the contrast agents 136 into the chamber 134. The visual representation of the contrast agents 136 in FIG. 3 is intended only to distinguish the contrast agents 136 from the chamber 134 in which they are disposed. According to various embodiments, the contrast agents 136 can be implemented as a gas, gel, or liquid, or as a combination of gases, gels, and/or liquids. Each of these materials can be selected independently to customize the appearance of the marker 130 in different imaging modalities and under different conditions, e.g., with or without contrast, and in various tissue types. For instance, if the marker 130 is to be visible in magnetic resonance (MR) and computed tomographic (CT) imaging modalities, the chamber 134 may contain a mixture of a gadolinium-DTPA MR contrast agent, such as MAGNEVIST® MR contrast agent, and an iodinated CT contrast agent, such as OMNIPAQUE™ CT contrast agent. The volume of contrast agent 136 in the chamber 134 may be maximized to promote visibility. Visibility is also promoted by matching the magnetic susceptibility of the contrast agent 136 and the magnetic susceptibility of the capsule 132. If it is further desired that the marker 130 be visible in an ultrasound imaging modality, the chamber 134 may also contain an air bubble. After the mixture is injected in the chamber 134, the capsule 132 is sealed.

In some embodiments, the capsule 132 itself, rather than multiple contrast agents 136, may provide visibility in certain imaging modalities. For example, the capsule 132 may be made of a radiopaque polymer that provides contrast in X-ray imaging modalities. As another example, a difference in acoustic impedance between the capsule 132 and the material in the chamber 134 will cause the marker 130 to reflect ultrasound waves, thereby promoting visibility in an ultrasound imaging modality. Further, if the magnetic susceptibility of the capsule 132 is similar to that of the material in the chamber 134 and to that of the surrounding tissue, visibility in MR imaging modalities will be improved due to reduction of T2 darkening.

The markers 100, 120, and 130 illustrated in FIGS. 1-3 can be used for imaging a location within a patient's body. One or more markers are implanted near the location via, for example, a biopsy cannula. The markers can be implanted using any of a variety of conventional techniques, including, but not limited to, non-invasive medical procedures, biopsy procedures, injection, and conventional surgical procedures. In addition, the markers can be guided to a desired anatomical site during implantation using one or more imaging modalities in which the markers are detectable. For example, implantation can be guided using MRI, CT, ultrasound, or other modalities.

An image of the location is then generated in an MRI modality. In addition, another image of the location can be generated in another imaging modality, such as a CT X-ray imaging modality. Other imaging modalities may be employed, such as ultrasound, X-ray, fluoroscopy, electrical impedance tomography, magnetic source imaging (MSI), magnetic resonance spectroscopy (MRS), magnetic resonance mammography (MRM), magnetic resonance angiography (MRA), magnetoelectroencephalography (MEG), laser optical imaging, electric potential tomography (EPT), brain electrical activity mapping (BEAM), arterial contrast injection angiography, digital subtraction angiography, positron emission tomography (PET), and single photon emission computed tomography (SPECT).

If multiple imaging modalities are employed, positional information for the area of the body that was imaged can be determined as a function of the images thus generated. For example, the images can be registered so as to align the coordinate systems of the images. In this way, any point in the imaged area of the body is made to correspond to identical addresses in each image. This registration process involves the use of rigid body transformation techniques, which in three-dimensional images requires knowledge of at least three points in each image. The markers described above may serve as fiducial markers to mark these points in the images. Accordingly, the fiducial markers can be used to correlate the spaces in each image, both with respect to physical space and with respect to the other images. In addition, the fiducial markers provide a constant frame of reference that is visible in each imaging modality to facilitate registration.

As demonstrated by the foregoing discussion, various embodiments may provide certain advantages, particularly in the context of imaging heterogeneous breast tissue. For instance, the use of a mixture of an MR contrast agent and a CT contrast agent may promote visibility in multiple imaging modalities, thus facilitating registering images obtained by multimodal imaging procedures. A contrast agent selected to produce an increase in signal intensity in an MR imaging modality may produce good visualization characteristics without also producing an excessive artifact and without interfering with MR spectroscopy or diffusion imaging. By producing an increase in signal intensity in MR imaging, the implantable tissue markers disclosed herein may be easier to see than conventional markers.

Because the contrast agents are sealed within the tube or capsule, they are at least substantially permanent and are not absorbed by the patient's body. Thus, multimodal imaging using the markers disclosed herein also allows a clinician to monitor an anatomical site over a period of time using images from multiple modalities, if desired. If the anatomical site in question requires treatment, the markers can be used to determine the precise location of the anatomical site and thus guide therapy. For example, markers can be implanted at a lesion site prior to removing the lesion to guide the procedure. After the lesion is removed, the markers can be used to monitor the site overtime.

It will be understood by those who practice the embodiments described herein and those skilled in the art that various modifications and improvements may be made without departing from the spirit and scope of the disclosed embodiments. For example, the markers disclosed herein may incorporate therapeutic agents, such as radioactive agents, anti-inflammatory agents, anti-microbial agents, hemostatic agents, biocompatible adhesives, proteins, stem cells, or other material. Such agents may be applied to an external surface of the markers or disposed within the internal chambers. Accordingly, the scope of protection afforded is to be determined solely by the claims and by the breadth of interpretation allowed by law.

Figure 7:
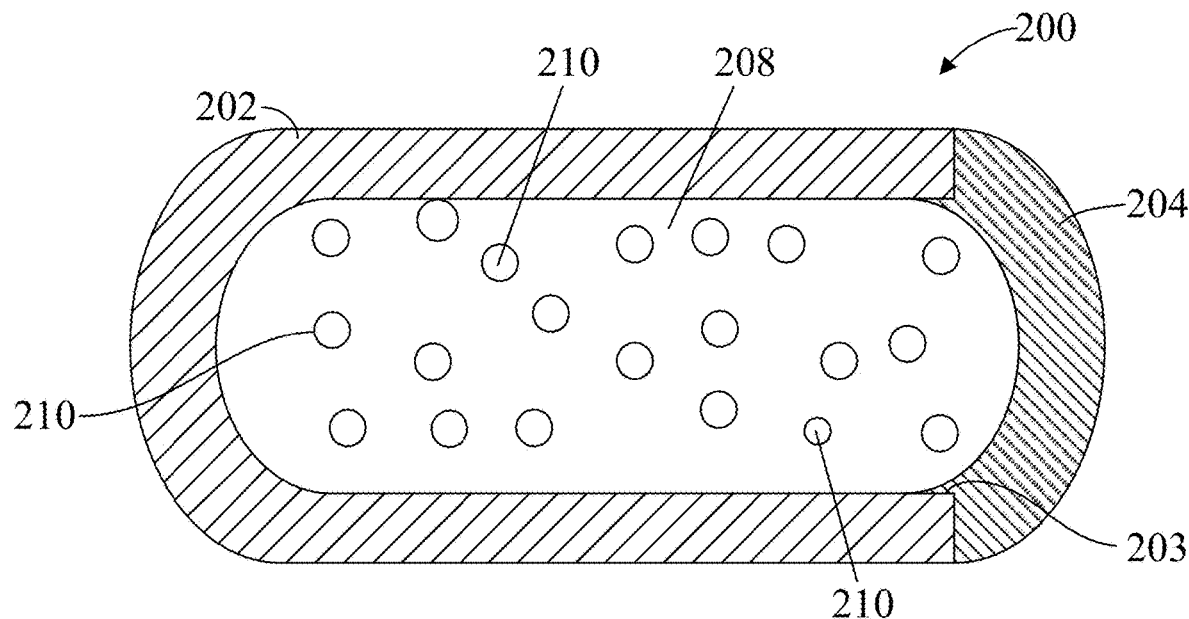
FIG. 7 is a sectional view of a tissue marker according to an embodiment.
Figure 8:
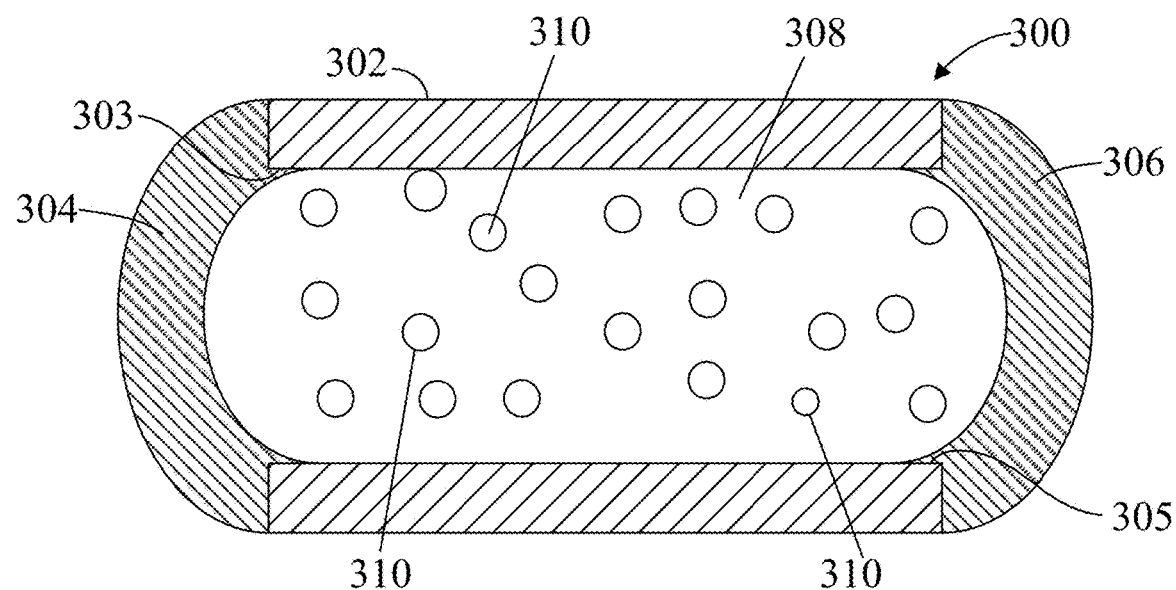
FIG. 8 is a sectional view of a tissue marker according to an embodiment.

Referring to FIGS. 7 and 8, additional examples of implantable radiographic markers 200, 300 are shown. The markers 200, 300, in various examples, can be formed from materials and in manners similar to those discussed herein.

Referring to FIG. 7, briefly, in some examples, the marker 200 includes a fully implantable, biocompatible container 202 formed from a nonbiodegradable solid material and defining an internal chamber 208. In this example, the container 202 includes an opening 203. In a further example, the container 202 is substantially vial-shaped. The marker 200, in an example, includes a lid portion 204 configured to be attached to the container 202 to close the opening 203. In an example, the lid portion 204 is configured to seal the opening 203. In an example, the marker 200 is sized for insertion via a biopsy cannula.

In some examples, one or more contrast agents 210 are introduced into the chamber 208. The opening 203, in an example, is sealed with the lid portion 204 to seal the contrast agent 210 within the chamber 208, in some examples, the opening 203 can be sealed in various ways, including press-fitting the lid portion 204 within the opening 203 of the container 202, using sealant or epoxy, or using other sealing techniques, such as, for instance ultrasonic welding of the lid portion 204 and the container 202. The visual representation of the contrast agents 210 in FIG. 7 is intended only to distinguish the contrast agents 210 from the chamber 208 in which they are disposed. According to various examples, the contrast agents 210 can be implemented as a gas, gel, or liquid, or as a combination of gases, gels, and/or liquids. Each of these materials can be selected independently to customize the appearance of the marker 200 in different imaging modalities and under different conditions, for instance, with or without contrast or in various tissue types. For instance, various contrast agents 210 or combinations of contrast agents 210, as described herein with respect to other examples, can be used for different imaging conditions, imaging modalities, tissue types, etc.

In an example, the marker 200 is formed by injection molding the container 202 and the lid portion 204. In another example, the marker 200 can be formed by micromachining. In a further example, the marker 200 can be encapsulated by a material, such as, for instance, silicone, PTFE, or another substance capable of performing as described herein. Such encapsulation, in various examples, can improve the seal of the marker 200; improve the bio-compatibility of the marker 200; can improve the surface properties of the marker 200, for instance, to facilitate deployment of the marker 200 through trocar or other device; or reduce bio-mobility of the marker 200 once it is implanted.

Referring to FIG. 8, briefly, in some examples, the marker 300 includes a fully implantable, biocompatible container 302 formed from a nonbiodegradable solid material and defining an internal chamber 308. In this example, the container 302 includes two openings 303, 305. In a further example, the container 302 is substantially tube-shaped. The marker 300, in an example, includes two lid portions 304, 306 configured to be attached to the container 302 to close the openings 303, 305. In an example, the lid portions 304, 306 are configured to seal the openings 303, 305. In an example, the marker 300 is sized for insertion via a biopsy cannula.

In some examples, one or more contrast agents 310 are introduced into the chamber 308. The openings 303, in an example, are sealed with the lid portions 304, 306 to seal the contrast agent 310 within the chamber 308. In some examples, the openings 303, 305 can be sealed in various ways, including press-fitting the lid portions 304, 306 within the openings 303, 305 of the container 302, using sealant or epoxy, or using other sealing techniques, such as, for instance ultrasonic welding of the lid portions 304, 306 and the container 302. The visual representation of the contrast agents 310 in FIG. 8 is intended only to distinguish the contrast agents 310 from the chamber 308 in which they are disposed. According to various examples, the contrast agents 310 can be implemented as a gas, gel, or liquid, or as a combination of gases, gels, and/or liquids. Each of these materials can be selected independently to customize the appearance of the marker 300 in different imaging modalities and under different conditions, for instance, with or without contrast or in various tissue types. For instance, various contrast agents 310 or combinations of contrast agents 310, as described herein with respect to other examples, can be used for different imaging conditions, imaging modalities, tissue types, etc.

In an example, the marker 300 is formed by injection molding the container 302 and the lid portions 304, 306. In another example, the marker 300 can be formed by micromachining. In a further example, the marker 300 can be encapsulated by a material, such as, for instance, silicone, PTFE, or another substance capable of performing as described herein. Such encapsulation, in various examples, can improve the seal of the marker 300; improve the bio-compatibility of the marker 300; can improve the surface properties of the marker 300, for instance, to facilitate deployment of the marker 300 through trocar or other device; or reduce bio-mobility of the marker 300 once it is implanted.

With reference to FIGS. 1-8, further examples include methods of manufacturing radiographic markers 100, 120, 130, 200, 300 capable of being permanently implanted in a living human or animal subject. In various examples, the fully implantable, biocompatible container 102, 122, 132, 202, 302 is formed from a nonbiodegradable solid material. In some examples, the container 102, 122, 132, 202, 302 is formed to define an internal chamber 108, 124, 134, 208, 308. In some examples, the contrast agent 110, 126, 136, 210, 310 is sealed within the internal chamber 108, 124, 134, 208, 308. In various examples, the contrast agent 110, 126, 136, 210, 310 is configured to produce a change in signal intensity in at least a magnetic resonance (MR) imaging modality with the marker 100, 120, 130, 200, 300 fully implanted in the subject. In an example, the solid material of the container 102, 122, 132, 202, 302 includes a first magnetic susceptibility and the contrast agent 110, 126, 136, 210, 310 includes a second magnetic susceptibility. In a further example, the solid material and the contrast agent 110, 126, 136, 210, 310 are configured such that the first and second magnetic susceptibilities are matched so that the first magnetic susceptibility is substantially equivalent to the second magnetic susceptibility. In some examples, the permanently implantable radiographic marker 100, 120, 130, 200, 300 is sized and shaped to fit within a lumen of a cannula configured to deliver the marker 100, 120, 130, 200, 300 to a fully implanted location within the subject.

In several examples, the method includes at least partially filling the internal chamber 108, 124, 134, 208, 308 with the contrast agent 110, 126, 136, 210, 310. Such filling can be accomplished in various manners including, but not limited to those described herein. In an example, the container 102, 122, 132, 202, 302 can be immersed within the contrast agent 110, 126, 136, 210, 310 to inhibit gas from being sealed within the internal chamber 108, 124, 134, 208, 308 in a further example, the container 102, 122, 132, 202, 302 is sealed while the container 102, 122, 132, 202, 302 is immersed in the contrast agent 110, 126, 136, 210, 310 to further inhibit unwanted materials from being sealed within the internal chamber 108, 124, 134, 208, 308 of the container 102, 122, 132, 202, 302. In an example, the container 102, 122, 132, 202, 302 can be immersed within a vat, receptacle, tank, etc. of the contrast agent 110, 126, 136, 210, 310 in order to lessen the amount of air or another gas from being present within the internal chamber 108, 124, 134, 208, 308 prior to sealing of the container 102, 122, 132, 202, 302. In some examples, the internal chamber 108, 124, 134, 208, 308 is at least partially filled with the contrast agent 110, 126, 136, 210, 310 with the container 102, 122, 132, 202, 302 within a chamber filled with a gas other than ambient air to inhibit ambient air from being sealed within the internal chamber 108, 124, 134, 208, 308. In an example, the chamber within which the container 102, 122, 132, 202, 302 is filled includes air or another gas at a pressure other than ambient pressure. For instance, the container 102, 122, 132, 202, 302 can be filled in a vacuum, in a high pressure environment, or in a pressure therebetween in some examples, the internal chamber 108, 124, 134, 208, 308 can be filled with the contrast agent 110, 126, 136, 210, 310 with the container 102, 122, 132, 202, 302 within a chamber substantially filled with a gas other than air. In a further example, the internal chamber 108, 124, 134, 208, 308 can be filled with the container 102, 122, 132, 202, 302 within the chamber substantially filled with nitrogen. For instance, in certain examples, oxygen (present in air) can be undesirable due to magnetic properties that could make susceptibility matching of the marker 100, 120, 130, 200, 300 more difficult than if oxygen were not present. In this example, filling of the container 102, 122, 132, 202, 302 with the contrast agent 110, 126, 136, 210, 310 within a nitrogen-filled chamber would cause residual gas bubbles within the container 102, 122, 132, 202, 302 to be nitrogen rather than oxygen, which can be more desirable in certain examples due to the different magnetic properties of nitrogen than those of oxygen. However, in other examples, the presence of oxygen within the container 102, 122, 132, 202, 302 can be desirable. In these examples, by adjusting the mixture of air or other gas or gases, the magnetic susceptibility and, therefore, the MRI visibility, of the marker 100, 120, 130, 200, 300 can be adjusted.

In some examples, the container 102, 122, 132, 202, 302 is vibrated during filling to aid in removal of gas bubbles from within the internal chamber 108, 124, 134, 208, 308 prior to sealing of the container 102, 122, 132, 202, 302. Such vibration can cause gas bubbles within the contrast agent 110, 126, 136, 210, 310 to rise out of the contrast agent 110, 126, 136, 210, 310 and toward an opening in the container 102, 122, 132, 202, 302, so that the gas bubbles can exit the container 102, 122, 132, 202, 302 prior to sealing of the container 102, 122, 132, 202, 302. In an example, the container 102, 122, 132, 202, 302 is ultrasonically vibrated in order to aid in removal of gas bubbles from within the internal chamber 108, 124, 134, 208, 308 prior to sealing of the container 102, 122, 132, 202, 302.

The various examples of filling of the container 102, 122, 132, 202, 302 described herein can be used to introduce or decrease amounts of various contrast agent materials within the internal chamber 108, 124, 134, 208, 308 of the container 102, 122, 132, 202, 302, based upon the desired mix of the contrast agent, the desired purity of the contrast agent, the desired response of the contrast agent in various imaging modalities, or the like. In this way, the filling environment and/or the contrast agent 110, 126, 136, 210, 310 within the container 102, 122, 132, 202, 302 can be controlled to tune the response of the marker 100, 120, 130, 200, 300 in one or more of various imaging modalities. The described examples of filling of the container 102, 122, 132, 202, 302 are meant to be illustrative and are not intended to be limiting. As such, additional techniques and methods of filling the container 102, 122, 132, 202, 302 are contemplated herein.

In some examples, the method includes mixing a first contrast agent configured to produce the change in signal intensity in the MR imaging modality and a second contrast agent configured to produce a signal in another imaging modality. In an example, the other imaging modality includes a computed tomographic (CT) X-ray imaging modality. In other examples, the other imaging modality includes one of an ultrasound imaging modality, an X-ray imaging modality, a fluoroscopy imaging modality, an electrical impedance tomographic imaging modality, a magnetic source imaging (MSI) modality, an magnetic resonance spectroscopic (MRS) modality, a magnetic resonance mammographic (MRM) modality, a magnetic resonance angiographic (MRA) modality, a magnetoelectroencephalographic (MEG) modality, a laser optical imaging modality, an electric potential tomographic (EPT) modality, a brain electrical activity mapping (BEAM) modality, an arterial contrast injection angiographic modality, a digital subtraction angiographic modality, a positron emission tomographic (PET) modality, and a single photon emission computed tomographic (SPECT) modality. In an example, the contrast agent 110, 126, 136, 210, 310 includes the mixture of the first and second contrast agents. In this example, the mixture of the first and second contrast agents is sealed within the internal chamber 108, 124, 134, 208, 308. In other examples, any number of contrast agents can be mixed together, depending upon the application for which the marker 100, 120, 130, 200, 300 is to be used. In an example, the first contrast agent includes a paramagnetic material. In another example, the first contrast agent includes gadolinium. In a further example, the second contrast agent includes iodine. In various examples, the contrast agent 110, 126, 136, 210, 310 includes at least one of a gas material, a liquid material, or a gel material.

In another example, the method includes sealing a therapeutic agent within the internal chamber 108, 124, 134, 208, 308.

In an example, the method includes forming the container 102, 122, 132, 202, 302 from a solid material configured to produce a signal in an imaging modality other than MR, including, but not limited to other imaging modalities described herein.

In various examples, the method includes forming the container 102, 122, 132, 202, 302 in various ways. In an example, the container 102, 122, 132, 202, 302 is molded. In a further example, the container 102, 122, 132, 202, 302 is injection molded. In a still further example, the container 102, 122, 132, 202, 302 is micromachined. The above examples are intended to be illustrative, not limiting, as it is contemplated that the container 102, 122, 132, 202, 302 can be formed in manners or using techniques other than those described herein, depending upon factors including the materials, size, shape, etc. of the marker 100, 120, 130, 200, 300.

In such examples, the container 102, 122, 132, 202, 302 can be formed from various materials. In some examples, the container 102, 122, 132, 202, 302 is formed from a polymeric material. In a further example, the container 102, 122, 132, 202, 302 is formed from a polyether material. In still further examples, the container 102, 122, 132, 202, 302 is formed from a material including at least one of polytetrafluoroethylene (PTFE), polyether ether ketone (PEEK), polysulfone, polyurethane, and polyethylene. In another example, the container 102, 122, 132, 202, 302 is formed from a silicone-based material. The above examples are intended to be illustrative, not limiting, as it is contemplated that the container 102, 122, 132, 202, 302 can be formed from materials other than those described herein, depending upon the use and desired properties of the marker 100, 120, 130, 200, 300.

In some examples, the method includes forming the tube 102 defining the first and second end portions 104, 106. In an example, the contrast agent 110 is sealed within the internal chamber 108 includes at least substantially sealing the first and second end portions 104, 106 using the biocompatible adhesive 112. In further examples, the tube 102 is formed from a solid material including at least one of a glass material, a ceramic material, a polymer material, silicone, or carbon fiber.

In some examples, the method includes forming a vial-shaped portion 202 of the container 202. In this example, the vial-shaped portion 202 includes the opening 203. In an example, the lid portion 204 of the container 202 is also formed. In this example, the lid portion 204 of the container 202 is configured to be attached at the opening 203 of the vial-shaped portion 202 of the container 202.

In some examples, the method includes forming a first portion 302 including at least two openings 303, 305. In this example, second and third portions 304, 306 are formed and are configured to be attached to the first portion 302 at the at least two openings 303, 305. In an example, the first portion 302 is substantially tube-shaped. In an example, the second and third portions 304, 306 are attached at the respective openings 303, 305 of the first portion 302 to seal the contrast agent 310 within the internal chamber 308. In other examples, the first portion includes other shapes, such as, but not limited to, substantially spherical, substantially ellipsoidal, substantially prismatic, etc. In other examples, the first portion can include more or less than two openings.

In some examples, the method includes coating the marker 100, 120, 130, 200, 300 to encapsulate the marker 100, 120, 130, 200, 300. In an example, the marker 100, 120, 130, 200, 300 is fully encapsulated with a material to improve the seal of the marker 100, 120, 130, 200, 300; improve the bio-compatibility of the marker 100, 120, 130, 200, 300; can improve the surface properties of the marker 100, 120, 130, 200, 300, for instance, to facilitate deployment of the marker 100, 120, 130, 200, 300 through trocar or other device; or reduce bio-mobility of the marker 100, 120, 130, 200, 300 once it is implanted. In an example, such encapsulation hermetically seals the marker 100, 120, 130, 200, 300. Various materials are contemplated for encapsulating the marker 100, 120, 130, 200, 300. For instance, in some examples, the marker 100, 120, 130, 200, 300 can be coated with a material including at least one of silicone or PTFE.

Figure 9:
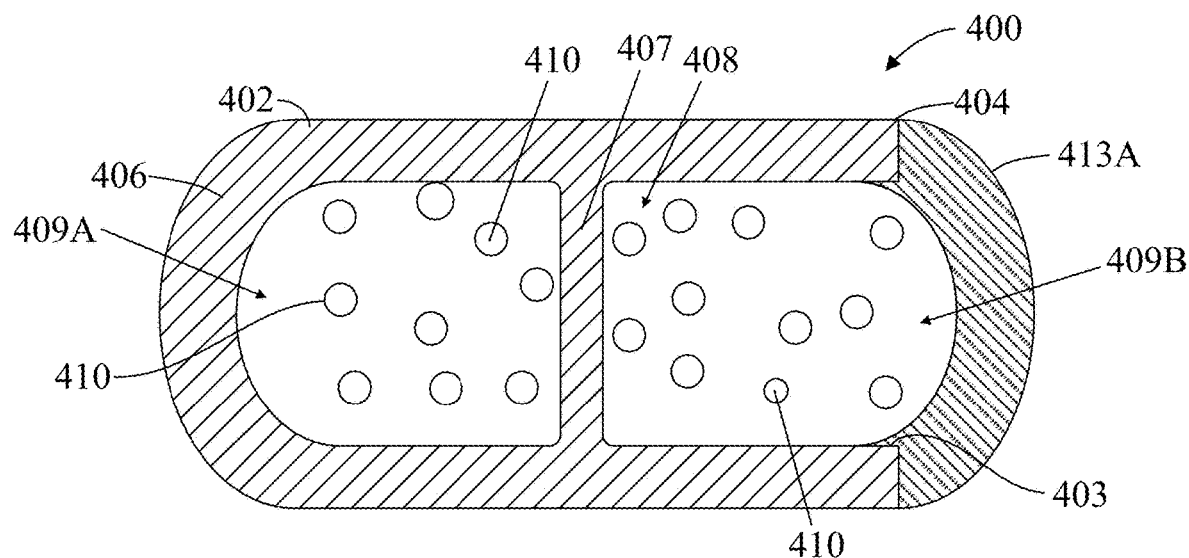
FIG. 9 is a sectional view of a tissue marker according to an embodiment.

Referring to FIG. 9, in an example, a marker 400 can comprise an outer wall 402 defining two end portions 404 and 406. The outer wall 402 can be formed from a non-biodegradable solid material and defining an internal chamber 408. In an example, the marker 400 can include an internal wall 407 dividing the internal chamber 408 into at least one of a first sub-chamber 409A and a second sub-chamber 409B. In at least one example, the marker 400 can include a second internal wall for further subdividing the internal chamber 408 into a plurality of sub-chambers. The first sub-chamber 409A or second sub-chamber 409B can contain a sensing medium detectable by an imaging modality, while the other sub-chamber 409A, 409B contains a sensing medium or a secondary component 411. The sensing medium in the other sub-chamber 409A, 409B can be the same sensing medium or a different sensing medium from the sensing medium within the first or second sub-chamber 409A.

In at least one example, the sensing mediums can include a contrast agent 410 as illustrated in FIG. 9. According to various examples, the contrast agents 410 can be implemented as a gas, gel, or liquid, or as a combination of gases, gels, and/or liquids. Each of these materials can be selected independently to customize the appearance of the marker 400 in different imaging modalities and under different conditions, for instance, with or without contrast or in various tissue types.

As illustrated in FIG. 9, the secondary component 411 can comprise a therapeutic composition, a sensor, or another feature. The therapeutic composition can comprise pharmacologic agents, biologic agents, radiative agents, and combinations thereof. In this configuration, the outer wall 402 or a portion thereof adjacent to the first or second sub-chamber 409A, 409B containing the therapeutic composition can be permeable to permit elution of the therapeutic composition out of the marker 400. In at least one example, a contrast agent 410 can be interspersed within the therapeutic composition such that the composition in the sub-chamber 409A, 409B is detectable by a sensing modality.

In an example, the sensor can comprise a sensor such as electrochemical or electronic sensors for monitoring at least one physiological condition. The sensor can have a transmitter for conveying the measured information to an external receiver. In an example, the sensor can have at least one of a passive radio frequency transmitter or a transponder. The physiological condition can comprise at least one of temperature, pH, tissue oxygen levels, and other physiological factors that may be indicative of metabolic function or specific disease state or suggestive of tumor necrosis, angiogenesis, and other biological processes, in this configuration, the outer wall 402 or a portion thereof adjacent to the first or second sub-chamber 409A, 409B containing the sensor can be permeable to permit physiological fluid to enter the first or second sub-chamber 409A, 409B to interact with the sensor.

In an example, the secondary component 411 can comprise structures or transponders such as REED microchips, uniquely shaped solid objects detectable under x-ray imaging modalities, and other identifying components that can be detected and identified by external imaging modalities.

Figure 10:
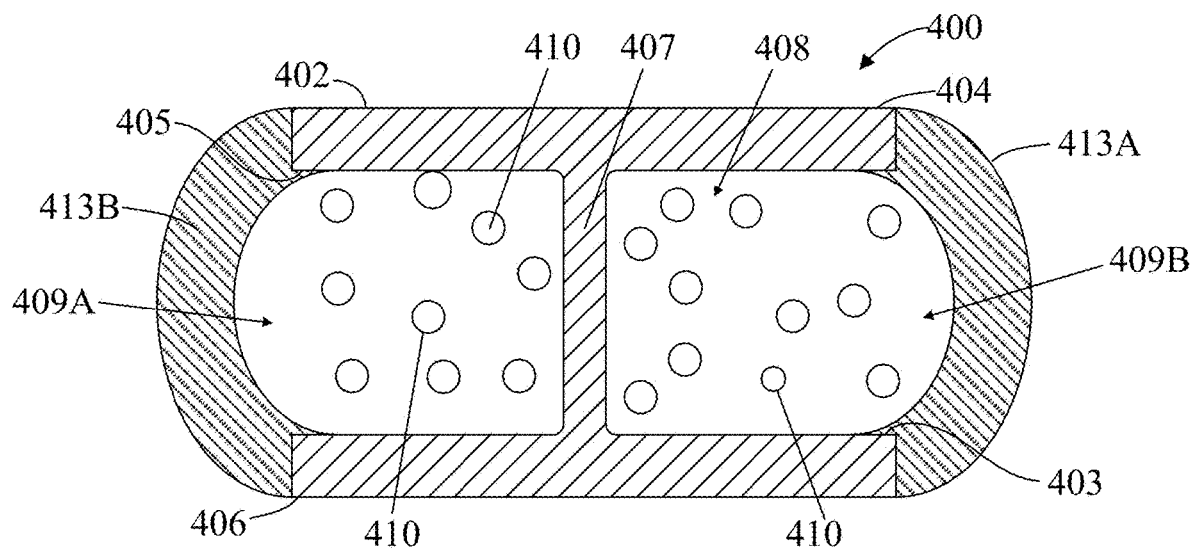
FIG. 10 is a sectional view of a tissue marker according to an embodiment.

In an example, the outer wall 402 can define a first opening 403 for accessing the first sub-chamber 409A. In this configuration, the marker 400 can include a first lid 413A for enclosing the first sub-chamber 409A. The secondary component or the sensing medium can be sealed in the second sub-chamber 409B. As illustrated in FIG. 10, in at least one example, the marker 400 can also include a second opening 405 accessing the second sub-chamber 409B. In this configuration, the marker 400 can include a second lid 413B for enclosing the first sub-chamber 409B. The first and second lids 413A, 413B are fused to the outer wall 402 with sealant, epoxy, ultrasonic welding, or other sealing technique.

VARIOUS NOTES & EXAMPLES

Example 1 is a permanently implantable radiographic marker, comprising: a biocompatible container having an outer wall defining an internal chamber and an internal wall positioned within the internal chamber to divide the internal chamber into a first sub-chamber and a second sub-chamber; a sensing medium positioned within the first sub-chamber; and a secondary component positioned within the second sub-chamber.

In Example 2, the subject matter of Example 1 optionally includes wherein the biocompatible container further comprises: a second internal wall positioned within the internal chamber to further divide the internal chamber into a plurality of sub-chambers.

In Example 3, the subject matter of any one or more of Examples 1-2 optionally include wherein the sensing medium is detectable by an imaging modality comprising at least one of MRI, ultrasound, x-ray, nuclear machine, infrared, fluorescence, and combinations thereof.

In Example 4, the subject matter of any one or more of Examples 1-3 optionally include wherein the secondary component comprises a sensor for measuring at least one physiological condition.

In Example 5, the subject matter of Example 4 optionally includes wherein the sensor is electrochemical; wherein at least a portion of the outer wall adjacent the second sub-chamber is permeable to permit at least one physiological fluid to permeate into the second sub-chamber.

In Example 6, the subject matter of any one or more of Examples 4-5 optionally include wherein the sensor is electronic.

In Example 7, the subject matter of any one or more of Examples 4-6 optionally include wherein the secondary component further comprises a transmitter for communicating measured physiological conditions.

In Example 8, the subject matter of any one or more of Examples 4-7 optionally include wherein the physiological condition comprises at least one of temperature, pH, and tissue oxygen levels.

In Example 9, the subject matter of any one or more of Examples 1-8 optionally include wherein the secondary component comprises a therapeutic composition.

In Example 10, the subject matter of Example undefined optionally includes, wherein the therapeutic composition comprises at least one of pharmacologic agents, biologic agents, radiative agents, and combinations thereof.

In Example 11, the subject matter of Example undefined optionally includes, wherein at least a portion of the outer wall adjacent the second sub-chamber is permeable to permit elution of the therapeutic composition from the marker.

In Example 12, the subject matter of Example undefined optionally includes, wherein the secondary component comprises at least one solid identifying component configured to provide an identifying signal when an external imaging modality is applied.

In Example 13, the subject matter of Example undefined optionally includes, wherein the outer wall comprises a solid material including at least one of a glass material, a ceramic material, a polymer material or a composite material.

In Example 14, the subject matter of Example undefined optionally includes, wherein at least one of the sensing medium and the secondary component contains a contrast agent.

Example 15 is a method of manufacturing a radiographic marker capable of being permanently implanted in a living human or animal subject, the method comprising: providing a fully implantable, biocompatible container formed from a non-biodegradable solid material, the fully implantable, biocompatible container defining an internal chamber divided into at least a first sub-chamber and a second sub-chamber by an internal wall; filling the first sub-chamber with the sensing medium for producing a change in signal intensity when exposed to an external imaging modality; placing a secondary component within the second sub-chamber; sealing the first and second sub-chambers.

In Example 16, the subject matter of Example 15 optionally includes wherein the sensing medium produces a signal detectable by an imaging modality comprising at least one of MRI, ultrasound, x-ray, nuclear machine, infrared, fluorescence, and combinations thereof.

In Example 17, the subject matter of any one or more of Examples 15-16 optionally include wherein the secondary component comprises at least one of a second sensing medium, a therapeutic composition, a sensor, an identifying component, and combinations thereof.

In Example 18, the subject matter of Example 17 optionally includes wherein at least a portion of the implantable, biocompatible container adjacent the second sub-chamber is permeable.

In Example 19, the subject matter of any one or more of Examples 15-18 optionally include removably connecting a lid portion to the outer wall for accessing at least one of the first sub-chamber and the second sub-chamber.

In Example 20, the subject matter of Example 19 optionally includes wherein the outer wall further comprises: Removably connecting a second lid portion to the outer wall for accessing the other of the first sub-chamber and the second sub-chamber.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 CFR. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. An implantable substantially permanent radiographic marker that allows a clinician to monitor an anatomical site over time, the radiographic marker comprising:
   a biocompatible container including a nonbiodegradable material, the biocompatible container having an internal chamber including a first sub-chamber and a second sub-chamber, wherein the first sub-chamber and the second sub-chamber are isolated by a non-biodegradable seal to sealingly isolate the first sub-chamber from the second sub-chamber;
   a sensing medium positioned within the first sub-chamber and enclosed by the biocompatible container to substantially permanently seal the sensing medium within the first sub-chamber, wherein the sensing medium includes one or more of a gas, a gel, or a liquid and the sensing medium is configured for detection by an imaging modality; and
   a secondary component positioned within the second sub-chamber, wherein the secondary component includes at least one different material characteristic than the sensing medium and the secondary component is substantially permanently sealingly isolated from the sensing medium by the non-biodegradable seal.

2. The radiographic marker of claim 1, wherein the sensing medium is hermetically sealed in the container by the nonbiodegradable material.

3. The radiographic marker of claim 1, wherein the imaging modality includes one or more of MRI, ultrasound, x-ray, nuclear machine, infrared, or fluorescence.

4. The radiographic marker of claim 1, wherein the secondary component comprises a sensor for measuring at least one physiological condition.

5. The radiographic marker of claim 4, wherein the sensor is electromechanical; and
   wherein the container includes an outer wall, and at least a portion of the outer wall adjacent the second sub-chamber is permeable to permit at least one physiological fluid to permeate into the second sub-chamber.

6. The radiographic marker of claim 4, wherein the sensor is electronic.

7. The radiographic marker of claim 4, wherein the secondary component further comprises a transmitter for communicating the measured at least one physiological condition.

8. The radiographic marker of claim 4, wherein the physiological condition comprises at least one of temperature, pH, and tissue oxygen levels.

9. The radiographic marker of claim 1, wherein the secondary component comprises a therapeutic composition including one or more of pharmacologic agents, biologic agents, radiative agents, and combinations thereof.

10. The radiographic marker of claim 1, wherein:
    the sensing medium is a first sensing medium;
    the imaging is a first imaging modality;
    the secondary component is a second sensing medium, and wherein the second sensing medium is configured for detection by a second imaging modality different than the first imaging modality.

11. The radiographic marker of claim 1, wherein the container includes an outer wall, and at least a portion of the outer wall adjacent the second sub-chamber is permeable to permit elution of a therapeutic composition from the marker.

12. The radiographic marker of claim 1, wherein the secondary component comprises at least one solid identifying component configured to provide an identifying signal when an external imaging modality is applied.

13. The radiographic marker of claim 1, wherein the biocompatible container includes:
    an internal container wall; and
    the seal extends from the internal container wall and across a longitudinal axis of the biocompatible container to isolate the first sub-chamber from the second sub-chamber and the seal precludes release of the contrast agent to allow the clinician to monitor the anatomical site over time.

14. The radiographic marker of claim 1, wherein at least one of the sensing medium and the secondary component contains a contrast agent.

15. A method of manufacturing a substantially permanent radiographic marker that allows a clinician to monitor an anatomical site over time, the method comprising:
    providing a fully implantable, biocompatible container formed from a non-biodegradable solid material, the fully implantable, biocompatible container defining an internal chamber divided into at least a first sub-chamber and a second sub-chamber, wherein the first sub-chamber is isolated from the second sub-chamber by a non-biodegradable seal to substantially permanently sealingly isolate the first sub-chamber from the second sub-chamber;

filling the first sub-chamber with a sensing medium including one or more of a gas, a gel, or a liquid and the sensing medium is configured to produce a change in signal intensity when exposed to an external imaging modality, wherein the sensing medium is enclosed within the first sub-chamber by the biocompatible container; and placing a secondary component within the second sub-chamber, wherein the secondary component includes at least one different material characteristic than the sensing medium and is substantially permanently sealingly isolated from the sensing medium by the non-biodegradable seal.

16. The method of claim 15, wherein the sensing medium produces a signal detectable by an imaging modality comprising at least one of MRI, ultrasound, x-ray, nuclear machine, infrared, or fluorescence.

17. The method of claim 15, wherein the secondary component comprises at least one of a second sensing medium, a therapeutic composition, a sensor, an identifying component, and combinations thereof.

18. The method of claim 17, wherein at least a portion of the implantable, biocompatible container adjacent the second sub-chamber is permeable.

19. The method of claim 15, wherein the container includes an outer wall and further comprising:

removably connecting a first lid portion to the outer wall for accessing one of the first sub-chamber or the second sub-chamber.

20. The method of claim 19, further comprising:

removably connecting a second lid portion to the outer wall for accessing an other one of the first sub-chamber or the second sub-chamber.

21. The radiographic marker of claim 1, wherein the secondary component includes a transponder.

* * * * *